United States Patent [19]

Ono et al.

[11] 3,968,165

[45] July 6, 1976

[54] PROCESS FOR PRODUCING ACROLEIN AND ACRYLIC ACID

[75] Inventors: Isao Ono; Tetsuo Iiguni; Mitsumasa Akashi, all of Shin Nanyo, Japan

[73] Assignee: Rohm and Haas Company, Philadelphia, Pa.

[22] Filed: Jan. 10, 1974

[21] Appl. No.: 432,388

Related U.S. Application Data

[62] Division of Ser. No. 215,906, Jan. 6, 1972, Pat. No. 3,786,000.

[52] U.S. Cl. .............................................. 260/604 R
[51] Int. Cl.² ........................................ C07C 45/04
[58] Field of Search ................................. 260/604 R

[56] References Cited
UNITED STATES PATENTS 3,236,782   2/1966   Koch ............................... 260/604 R
3,522,299   7/1970   Takenaka et al. ............... 260/604 R

FOREIGN PATENTS OR APPLICATIONS 873,712   7/1961   United Kingdom ............. 260/604 R Primary Examiner—James O. Thomas, Jr.
Assistant Examiner—W. B. Lone

[57] ABSTRACT

A process for producing acrolein which comprises catalytic oxidizing propylene in the vapor phase with oxygen and steam in the presence of novel catalyst, having superior nature in activity, and composed of oxides of Mo, Co, Fe, Bi, and Sn with or without one or more of Al, Ni, W, Cr, In, and Nb, is disclosed.

10 Claims, No Drawings

PROCESS FOR PRODUCING ACROLEIN AND ACRYLIC ACID

This is a division of application Ser. No. 215,906, filed Jan. 6, 1972, now U.S. Pat. No. 3,786,000.

BACKGROUND OF THE INVENTION

1. Field of the Invention

The present invention relates to a process for producing acrolein which comprises catalytic oxidization of propylene in the vapor phase with a gas containing oxygen and steam, in the presence of an oxidizing catalyst which comprises molybdenum, cobalt, iron, bismuth, and tin or, besides tin, by adding one or more elements selected from a group consisting of aluminum, nickel, tungsten, chromium, indium and niobium.

2. Description of the Prior Art

Similar catalysts are cited in Japanese Patent Publication No. 6245/69; Mo - Co / Ni - Fe - Bi and Mo - Co / Ni - Fe - Bi - P. The inventors, after detailed investigation, have found that a catalyst produced by adding tin and, optionally, one or more elements selected from a group consisting of aluminum, nickel, tungsten, chromium, indium and niobium gives a much improved catalyst. For example, in comparison with the catalyst cited in Japanese Patent Publication No. 6245/69, the space time yield of acrolein is increased by more than 100 percent under the same conditions of reaction. This is illustrated by comparison in the examples.

DESCRIPTION OF THE INVENTION

In accordance with the present invention, by employing a catalyst comprising oxides of the metallic elements of molybdenum, cobalt, iron, bismuth, and tin and, optionally, one or more elements selected from the group consisting of aluminum, nickel, tungsten, chromium, indium and niobium, propylene can be advantageously oxidized in the vapor phase with steam and air, or other gas containing oxygen, under ambient or elevated pressures, at a reaction temperature of 250° to 450° C.

The characteristics of the catalyst of the present invention are, for example:

1. sufficient activity at relatively low temperatures,
2. the space time yield is relatively high,
3. selectivity for acrolein is high,
4. since the catalyst has little activity in the oxidation of acrolein, even for high conversion of propylene, high selectivity for acrolein can be maintained.

The composition of the catalyst expressed by general formula in atomic numbers are as follows:

$$Mo_a \quad Co_b \quad Fe_c \quad Bi_d \quad A_e \quad O_f$$

wherein $a$ is equal to 12, and the values of $a$, $b$, $c$, $d$, $e$, and $f$ are, respectively, $b=7-12$, $c=0.3-4$, $d=0.4-2.5$, $e=0.1-3$, and $f=47-73$. "A" is composed of tin alone or a composite system of tin with the addition of one or more elements selected from the group consisting of aluminum, nickel, tungsten, chromium, indium and niobium. The minimum amount of tin in atomic amount is 0.1. In employing the catalyst in accordance with this invention, it can be employed as is, or may be used with a carrier or support like diatomaceous earth or alumina.

In producing the catalyst, various methods of preparation can be utilized. It is desirable that each of the essential elements is used in the form of their respective salts. These ingredients, after they are mixed in the atomic ratio of the elements above mentioned, are heated in aqueous solution or suspension with stirring to ensure complete reaction, and with or without a carrier or diluent, and after drying, are calcined at 450° to 550° C. for several hours, for example, 6 hours. The calcined materials thus produced can be employed in the condition as is, or it can be used after pressure molding to strengthen the catalyst.

In the method of using the catalyst, it is desirable that the temperature of reaction be maintained at 250° to 450° C., more preferably at 280° to 370° C. Though apparent contact time of the reactants varies according to the reaction temperature and composition of the feed gas, a range of 0.5 to 15 seconds is suitable. The composition of the feed gas varies over a wide range, with amounts in the ranges of 1 to 15 mol percent of propylene, 20 to 90 mol percent of air, and 5 to 50 mole percent of steam being preferred.

Reactors of either fixed bed or moving bed type can be used, but in each case, it is necessary to select catalyst carriers, forms of catalyst and method of preparation of the catalyst suitable to the reactor used.

By using catalyst systems in accordance with the present invention, acrolein can be produced selectively by oxidation of propylene very efficiently, at relatively low temperatures, with a gas mixture comprising oxygen and steam.

Conversion of propylene and selectivity for acrolein and acrylic acid are defined as follows:

$$\text{Conversion (\%) for propylene} = \frac{\text{Mols of propylene converted}}{\text{Mols of fed propylene}} \times 100$$

$$\text{Selectivity (\%) for acrolein} = \frac{\text{Mols of acrolein obtained}}{\text{Mols of propylene converted}} \times 100$$

$$\text{Selectivity (\%) for acrylic acid} = \frac{\text{Mols of acrylic acid obtained}}{\text{Mols of propylene converted}} \times 100$$

In the following, the present invention will be illustrated by examples and by examples of prior art catalysts for comparison.

EXAMPLE 1

62.72 g. of ammonium molybdate [$(NH_4)_6Mo_7O_{24}\cdot 4H_2O$], and 2.32 g. of ammmonium tungstate [$(NH_4)_{10}W_{12}O_{41}\cdot 5H_2O$] are dissolved in 300 ml. of water with the addition of 3.71 g. of stannic chloride [$SnCl_4\cdot 3H_2O$]. This mixture is referred to as Solution A.

86.14 g. of cobalt nitrate [$Co(NO_3)_2\cdot 6H_2O$], 3.14 g. of indium nitrate [$In(NO_3)_3\cdot 3H_2O$], and 11.94 g. of ferric nitrate [$Fe(NO_3)_3\cdot 9H_2O$] are dissolved in 40 ml. of water and to this solution, 14.37 g. of bismuth nitrate [$Bi(NO_3)_3\cdot 5H_2O$] dissolved in dilute nitric acid consisting of 1.41 ml. concentrated nitric acid and 10.6 ml. of water, is added. This mixture is referred to as Solution B.

After Solution B is added to Solution A with agitation and allowed to react, 10 g. of diatomaceous earth as a carrier is added, and the mixture is concentrated with agitation and heating. The damp mixture is molded to form particles or pellets of cylindrical shape, 5 mm. × 5 mm. in size, by means of perforated plates. After drying at 130° C. for 20 hours, the particles are calcined at 520° C. for 6 hours.

Approximate composition of the catalyst thus obtained is as follows: 90 wt. percent of $Mo_{12}Co_{10}Fe_1Bi_1Sn_{0.4}In_{0.3}W_{0.3}O_{56}$ and 10 wt. percent of diatomaceous earth as a carrier.

25 ml. of the above mentioned catalyst is packed in a U-shaped stainless steel reactor of 20 mm. inner diameter in a niter bath. A gaseous mixture consisting of 5 percent of propylene, 60 percent of air and 35 percent of steam, all by volume, is supplied at the rate of 635 ml./min., fed at ambient or normal temperature and pressure (NTP) and caused to react at a reaction temperature of 350° C. Conversion of propylene is 90.8 percent, selectivity for acrolein is 81.5 percent, and selectivity for acrylic acid is 9.4 percent. In addition, small quantities of acetic acid, carbon dioxide and carbon monoxide are obtained as by-products. The space time yield of acrolein is 2.51 mol./1.-hour.

EXAMPLE 2

64.04 g. of ammonium molybdate and 2.36 g. of ammonium tungstate are dissolved in 300 ml. of water, and to this solution 2.86 g. of stannic chloride is added and dissolved therein. This mixture is referred to as Solution A.

To a solution prepared by dissolving 87.93 g. of cobalt nitrate, 3.22 g. of indium nitrate, and 4.86 g. of ferric nitrate dissolved in 40 ml. of water, a solution in which 14.66 g. of bismuth nitrate is dissolved in a dilute nitric acid solution consisting of 1.40 ml. of concentrated nitric acid and 10.5 ml. of water, is added. This mixture is referred to as Solution B.

After Solution B is added to Solution A with agitation and allowed to react, 10 g. of diatomaceous earth as a carrier is added and concentrated in agitation and heating. Pellets are formed as in Example 1. The approximate composition of the catalyst thus obtained is as follows: 90 wt. percent of $Mo_{12}Co_{10}Fe_{0.4}Bi_1Sn_{0.3}In_{0.3}W_{0.3}O_{55}$ and 10 wt. percent of diatomaceous earth as a carrier.

47.5 ml. of the catalyst is packed in the reactor as in Example 1, heated in a niter bath, and a gas mixture consisting of 5 percent of propylene, 60 percent of air, and 35 percent of steam, by volume, is supplied at a rate of 635 ml./min. (NTP) and reacted at a temperature of 350° C. Conversion of propylene is 88.9 percent, selectivity for acrolein is 83.2 percent, and selectivity for acrylic acid is 8.0 percent. In addition, small quantities of acetic acid, carbon dioxide, and carbon monoxide are produced as by-products. The space time yield of acrolein is 1.32 mol./1.-hour.

EXAMPLES 3 – 6

Catalysts of the compositions shown in Table I are prepared in accordance with the method of Example 1, and they are packed in the reactor of Example 1. While being heated in a niter bath, a gas mixture consisting of 5 percent of propylene, 60 percent of air, and 35 percent of steam, by volume, are supplied at the rate of 635 ml./min. (NTP), the quantity of catalyst being such as to achieve conversion of propylene at about 90 percent. The results are shown in Table II. The temperature is maintained at about 350° C.

TABLE I

| Example No. | Composition of Catalyst | |
|---|---|---|
| 3 | $Mo_{12}Co_{10}Fe_1Bi_1Sn_{0.04}In_{0.03}W_{0.03}O_{54}$ | 90 wt. % + Diatomaceous earth 10 wt. % |
| 4 | $Mo_{12}Co_{10}Fe_1Bi_1Sn_{0.3}In_{0.2}O_{55}$ | " |
| 5 | $Mo_{12}Co_{10}Fe_1Bi_1Sn_{0.5}W_{0.5}O_{56.5}$ | " |
| 6 | $Mo_{12}Co_{10}Fe_1Bi_1Sn_1In_1W_1O_{60.5}$ | " |

TABLE II

Reaction Results

| Example No. | Quantity of Packed Catalyst (ml.) | Reaction Temperature (°C.) | Propylene Conversion (%) | Acrolein Selectivity (%) | Acrylic Acid Selectivity (%) | Acrolein Space Time Yield (mol/1.-hr.) |
|---|---|---|---|---|---|---|
| 3 | 33.8 | 350 | 89.0 | 82.4 | 10.2 | 1.84 |
| 4 | 36.2 | 350 | 87.5 | 75.6 | 9.4 | 1.55 |
| 5 | 30 | 350 | 90.1 | 81.3 | 10.5 | 2.07 |
| 6 | 45 | 350 | 88.3 | 78.7 | 9.1 | 1.31 |

EXAMPLE 7

Catalysts shown in Table III are produced in accordance with the method of producing the catalyst in Example 1, the catalysts are packed in the reactor cited in Example 1, heated in a niter bath, and a gas mixture consisting of 5 percent of propylene, 60 percent of air, and 35 percent of steam is supplied, the quantity of catalyst and the flow of gas mixture being adjusted to achieve conversion of propylene at about 90 percent. The results are shown in Table IV. These catalysts are considerably lower in activity compared with those of the present invention, and give a low space time yield of acrolein. The gas mixture is fed at about 635 ml./min. and the reaction temperature was at about 350° C.

TABLE III

| Comparison Example No. | Composition of Catalyst | |
|---|---|---|
| 1 | $Mo_{12}Co_{10}Fe_1Bi_1O_{54}$ | 90 wt. % + Diatomaceous earth 10 wt. % |
| 2 | $Mo_{12}Co_{10}Fe_{0.4}Bi_1O_{53}$ | " |
| 3 | $Mo_{12}Co_4Ni_{4.5}Fe_1Bi_1P_{0.08}O_{51.9}$ | " |

TABLE IV

Reaction Results

| Comparison Example No. | Quantity of Packed Catalyst (ml.) | Reaction Temperature (°C.) | Flow of Mixed Gas (ml./min.) (NTP) | Propylene Conversion (%) | Acrolein Selectivity (%) | Acrylic Acid Selectivity (%) | Acrolein Space Time Yield (mol./l.-hr.) |
|---|---|---|---|---|---|---|---|
| 1 | 50 | 350 | 635 | 88.7 | 79.1 | 7.5 | 1.19 |
| 2 | 47.5 | 350 | 226 | 89.2 | 77.5 | 8.9 | 0.44 |
| 3 | 50 | 350 | 580 | 87.6 | 76.8 | 9.5 | 1.05 |

EXAMPLES 8 – 18

After preparing catalysts of the compositions shown in Table V using the same method as Example 1, they are packed in the reactor of Example 1, heated in a niter bath, and a gas mixture consisting of 5 percent of propylene, 60 percent of air, and 35 percent of steam is supplied at a rate of 635 ml./min. (NTP). The reaction temperature was at about 350° C. The results are shown in Table VI.

TABLE V

| Example No. | Composition of Catalyst | |
|---|---|---|
| 8 | $Mo_{12}Co_{10}Fe_1Bi_1Sn_1O_{56}$ | 90 wt. % + Diatomaceous earth 10 wt. % |
| 9 | $Mo_{12}Co_{10}Fe_2Bi_2Sn_{0.2}O_{57.4}$ | " |
| 10 | $Mo_{12}Co_8Fe_2Bi_1Sn_{0.4}Al_{0.3}Ni_{0.2}O_{54}$ | " |
| 11 | $Mo_{12}Co_{11}Fe_2Bi_1Sn_{0.5}Al_{0.5}O_{58.7}$ | " |
| 12 | $Mo_{12}Co_{11}Fe_2Bi_{0.5}Sn_{0.4}Al_{0.3}Cr_{0.3}O_{58.9}$ | " |
| 13 | $Mo_{12}Co_9Fe_2Bi_1Sn_{0.4}Al_{0.4}W_{0.3}O_{57.3}$ | " |
| 14 | $Mo_{12}Co_7Fe_3Bi_1Sn_{0.5}Ni_{0.4}O_{54}$ | " |
| 15 | $Mo_{12}Co_{10}Fe_1Bi_{2.5}Sn_{0.4}In_{0.3}Ni_{0.3}O_{57.9}$ | " |
| 16 | $Mo_{12}Co_{10}Fe_1Bi_1Sn_{0.5}Nb_{0.3}Ni_{0.2}O_{56}$ | " |
| 17 | $Mo_{12}Co_{10}Fe_1Bi_1Sn_{0.4}Nb_{0.3}W_{0.4}O_{56.7}$ | " |
| 18 | $Mo_{12}Co_{10}Fe_2Bi_1Sn_{0.3}Al_{0.3}Nb_{0.3}In_{0.2}O_{57.6}$ | " |

TABLE VI

Reaction Results

| Example No. | Quantity of Packed Catalyst (ml.) | Reaction Temperature (°C.) | Propylene Conversion (%) | Acrolein Selectivity (%) | Acrylic Acid Selectivity (%) | Acrolein Space Time Yield (mol./l.-hr.) |
|---|---|---|---|---|---|---|
| 8 | 33 | 350 | 90.3 | 80.4 | 8.1 | 1.86 |
| 9 | 43 | 350 | 89.5 | 78.8 | 7.8 | 1.39 |
| 10 | 30 | 350 | 90.8 | 78.9 | 9.7 | 2.03 |
| 11 | 37.5 | 350 | 89.4 | 79.2 | 8.5 | 1.60 |
| 12 | 35 | 350 | 87.1 | 76.5 | 7.4 | 1.61 |
| 13 | 34 | 350 | 87.9 | 81.2 | 9.2 | 1.80 |
| 14 | 40 | 350 | 86.4 | 78.3 | 7.5 | 1.44 |
| 15 | 33 | 350 | 89.4 | 77.6 | 9.3 | 1.80 |
| 16 | 31 | 350 | 86.6 | 80.4 | 8.6 | 1.89 |
| 17 | 30 | 350 | 90.4 | 79.5 | 7.9 | 2.03 |
| 18 | 31 | 350 | 90.2 | 79.9 | 9.4 | 1.96 |

What is claimed is:

1. A process for producing acrolein which comprises catalytic oxidizing propylene with a gas containing oxygen and steam in the vapor phase, at a temperature of 250 to 450°C, employing a calcined catalyst having the general composition of $Mo_a\ Co_b\ Fe_c\ Bi_d\ A_e\ O_f$, wherein $a$, $b$, $c$, $d$, $e$, and $f$ in the above formula are respectively the atomic amounts of each element, and when $a$ is equal to 12, the values of $b$, $c$, $d$, $e$, and $f$ have the respective ranges, $b=7-12$, $c=0.3-4$, $d=0.4-2.5$, $e=0.1-3$, $f=47-73$, and A is composed of tin alone or a composite system of tin and one or more elements selected from a group consisting of aluminum, nickel, tungsten, chromium, indium and niobium, the minimum content of tin in A being in the atomic amount of 0.1.

2. The process of claim 1 in which the catalyst is used as a fixed bed, and the feed gas contains 1 to 15 mol percent of propylene, 20 to 90 mol percent of air, and 5 to 50 mol percent of steam.

3. The process of claim 2 in which said temperature is 280° to 370° C.

4. The process of claim 1 in which A is composed of tin and aluminum.

5. The process of claim 1 in which A is composed of tin and nickel.

6. The process of claim 1 in which A is composed of tin and tungsten.

7. The process of claim 1 in which A is composed of tin and chromium.

8. The process of claim 1 in which A is composed of tin and indium.

9. The process of claim 1 in which A is composed of tin and niobium.

10. The process of claim 1 in which A is composed of tin.

* * * * *